US007871400B2

(12) United States Patent
Sablone et al.

(10) Patent No.: US 7,871,400 B2
(45) Date of Patent: Jan. 18, 2011

(54) SIDE PANEL FOR SANITARY ARTICLES, CORRESPONDING SANITARY ARTICLE AND METHOD OF PRODUCING SAME

(75) Inventors: Gabriele Sablone, Montesilvano (IT); Massimiliano Lombardi, Montesilvano (IT); Cristian Giuliani, Pineto (IT); Dario Galante, Vasto (IT)

(73) Assignee: Fameccanica.Data S.p.A., Sambuceto di San Giovanni Teatino (Chieti) (IT)

( * ) Notice: Subject to any disclaimer, the term of this patent is extended or adjusted under 35 U.S.C. 154(b) by 859 days.

(21) Appl. No.: 11/695,805

(22) Filed: Apr. 3, 2007

(65) Prior Publication Data

US 2008/0161766 A1 Jul. 3, 2008

(30) Foreign Application Priority Data

Jan. 2, 2007 (EP) ................................. 07425002

(51) Int. Cl.
*A61F 13/15* (2006.01)
*A61F 13/20* (2006.01)

(52) U.S. Cl. ................................. 604/385.01; 604/396

(58) Field of Classification Search ................. 604/358, 604/367, 385.01, 396, 386–387
See application file for complete search history.

(56) References Cited

U.S. PATENT DOCUMENTS 5,683,533 A * 11/1997 Keighley et al. ............ 156/204
5,705,013 A * 1/1998 Nease et al. ................ 156/260
6,572,595 B1 6/2003 Klemp et al.
6,730,189 B1 5/2004 Franzmann et al.

(Continued)

FOREIGN PATENT DOCUMENTS

EP 0669121 B1 6/1999

(Continued)

OTHER PUBLICATIONS

European Search Report for corresponding European application No. 07425002.8 dated May 11, 2007.

*Primary Examiner*—Michele Kidwell
(74) *Attorney, Agent, or Firm*—Heslin Rothenberg Farley & Mesiti P.C.; Victor A. Cardona, Esq.

(57) ABSTRACT

Described herein is a side panel for sanitary articles that can be worn as pants, such as baby diapers or sanitary towels, with a main body, which can assume a general U-shaped configuration, with end parts arranged on the front and on the back of the body of the user, and with at least one aforesaid side panel for connecting the aforesaid end parts on each side of the user. The side panel has an as a whole tapered pattern starting from a proximal edge to be fixed on the main body of the article and a distal edge carrying a connection formation for closing the article itself around the waistline of the user. The panel has, in connection with the proximal edge and distal edge, two end sides inclined with respect to the general direction of extension of the aforesaid proximal edge and distal edge. The end sides have profiles such that the side panel is juxtaposable without any solution of continuity in a position corresponding to said end sides with two homologous side panels rotated through 180° in the general plane of extension of the panel. Each connection formation is extendable in a distal direction beyond the distal edge of the panel.

7 Claims, 7 Drawing Sheets b
8
3
5
7
6
a
2
b'
3
6
8
7
T
5
r
x
x
a'
r

U.S. PATENT DOCUMENTS

| | | | |
|---|---|---|---|
| 6,994,761 | B2 | 2/2006 | Klemp et al. |
| 2004/0245069 | A1 | 12/2004 | Hook et al. |

FOREIGN PATENT DOCUMENTS

| | | | |
|---|---|---|---|
| EP | 0997123 | A1 | 5/2000 |
| EP | 1179495 | A1 | 2/2002 |
| EP | 11477068 | A1 | 8/2004 |
| EP | 1719484 | A1 | 11/2006 |
| EP | 1736272 | A1 | 12/2006 |
| FR | 2644694 | A1 | 9/1990 |
| WO | WO95/17871 | | 7/1995 |
| WO | WO 96/24319 | | 8/1996 |
| WO | WO 98/14156 | | 4/1998 |
| WO | WO 97/32552 | | 12/2004 |
| WO | WO 2006/063029 | A1 | 6/2006 |

* cited by examiner

6
T
7
3
x
r
a'
b'
8
x
r
5
2

3
5
8
b
a
6
7

7
3
P1

SIDE PANEL FOR SANITARY ARTICLES, CORRESPONDING SANITARY ARTICLE AND METHOD OF PRODUCING SAME

CROSS-REFERENCE TO RELATED APPLICATIONS

This application claims priority from European Patent Application No. 07425002.8, filed on Jan. 2, 2007, the entire disclosure of which is incorporated herein by reference.

FIELD OF THE INVENTION

The present invention relates in general to sanitary articles of the type that can be worn as pants. This designation is used herein in its widest sense, such as to comprise, for example, diapers for babies, including diapers of the pre-fastened type (of the type commonly referred to as "training pants") and sanitary towels for incontinence.

DESCRIPTION OF THE RELATED ART

Already for some years now, the sector of sanitary articles that can be worn as pants has undergone a substantial modification, above all as regards the structure of the article.

The guideline that has for several years been directing designers of absorbent articles (in particular, as regards baby diapers) is that of rendering the articles increasingly comfortable to wear.

In the pursuit of this objective, basically two technological lines of approach have been developed.

The first line concentrates upon the reduction of the volume of the absorbent core, this being pursued by using increasingly larger amounts of superabsorbent material, sometimes even abandoning altogether traditional absorbent materials (mattresses made of cellulose and/or artificial fibres) in favour of superabsorbent material.

The second approach concentrates instead upon the modification of the structure (so-called "chassis") of the article itself, which is pursued abandoning the hourglass shape traditionally adopted for articles of this kind to pass to an as a whole T shape, where the central part or stem of the T reproduces the traditional structure of the absorbent article (topsheet, backsheet, and absorbent core set in between), whilst at one end of said central part two side panels are present, the function of which is basically that of closing the sanitary article around the waist of the user, by connecting to one another the opposite ends of the central portion, which is set to form a hollow shape or U shape around the perineal region of the user.

Examples of structures of sanitary articles inspired by said approach are illustrated, for example, in the document No. EP-A-0 669 121 or in the document No. WO-A-95/17871.

The side panels are elasticated closing systems that are particularly complex and sophisticated. To meet completely the needs of use, the side panel must both perform functions of a structural nature (enabling closing of the sanitary article around the legs and around the region of the waist of the user and ensuring the maximum degree of comfort of wear) and enable transpiration, preventing any undesirable phenomena of maceration and scuffing of the skin of the user due to local accumulation of moisture.

The patent literature (of which the documents cited previously evidently constitute merely a very small sample) describes an ample range of shapes and structures of side panels.

To guarantee a good comfort of wear, it has up to now been deemed that the panel should present the outer edge with respect to the article (the top one in the position of use) perpendicular to the longitudinal axis of the article (in what follows, for reasons of simplicity, reference will be made above all to diapers for babies), and the inner edge (the bottom one in the position of use) forming an obtuse angle with the longitudinal axis of the article. From this consideration there arises the fact that the two edges, top and bottom, of the side panel do not form an angle of the same amplitude with the central body of the nappy. In other words, the side panel usually has an asymmetrical conformation.

At the moment, the side panels most appreciated by the market are the ones with an anatomical shape, provided with an independent closing element that can be opened, as occurs in the case of the closing systems that adopt a strip or adhesive label traditionally used in articles with a general hourglass conformation.

According to the needs outlined above, the materials commonly used for manufacturing the side panels in question are rather costly.

The above fact ends up by penalizing significantly the technologies that, for making the side panels, envisage starting from a web or strip of raw material, on the sides of which cuts are made shaped with a contour complementary to the contour that it is desired to impart on the side panels.

The main negative aspect of this solution lies in the cost involved, in so far as a very significant part of raw material—which is very costly—is inevitably bound to be discarded.

In general, it should in itself be considered known that, given that it is necessary to cut shaped elements out of a strip or web of raw material, it is possible to select profiles of the elements in question such as to create a situation of geometrical complementarity of the contour of said elements. For example, the document No. FR-A-2 644 694 discloses a solution in which, to produce absorbent sanitary pads or pantie liners for women of the type "with flaps", the starting point is a web or strip that is cut out lengthwise according to an approximately sinusoidal path of cutting. The two half-strips thus obtained are then turned over and connected back to back so as to obtain a weblike material with the desired contouring, without giving rise to processing waste.

An intrinsic drawback of this type of solution lies, however, in the fact that to the individual elements/articles thus formed there cannot be associated projecting connection elements, if not after the individual articles or elements have been cut out. This limits to a major extent the possibility of choice of the closing elements just to hook-and-loop elements.

OBJECT AND SUMMARY OF THE INVENTION

The prior art to which reference has been made previously thus leaves unresolved at least one essential problem, i.e., that of providing side panels for sanitary articles that, on the one hand, can be produced without generating process waste of the costly material of which they are made and, on the other, are suited to being equipped (already before cutting of the individual element) with projecting closing elements, such as, for example, adhesive labels or contact (hook-and-loop) labels projecting from the side panel.

According to the present invention, said object is achieved thanks to a side panel for sanitary articles that can be worn as pants having the characteristics recalled in claim 1. Advantageous developments of the invention form the subject of the subordinate claims. The invention also relates to a corresponding sanitary article, as well as to a corresponding method for the production (and application) of said side panels.

The claims form an integral part of the disclosure of the invention provided herein.

The solution described herein enables manufacture of sanitary articles provided with side panels of the type described previously without any processing waste as regards the material constituting the side panels and without any particular limitations as regards the closing formations that can be applied to said side panels. This is accompanied by the additional advantage of being able to carry out in a convenient way, basically via software, change of format, i.e., adaptation of the equipment designed for the production and application of the side panels in question to different formats of article.

BRIEF DESCRIPTION OF THE ANNEXED DRAWINGS

The invention will now be described, purely by way of non-limiting example, with reference to the annexed plate of drawings, in which.

Figure 2:
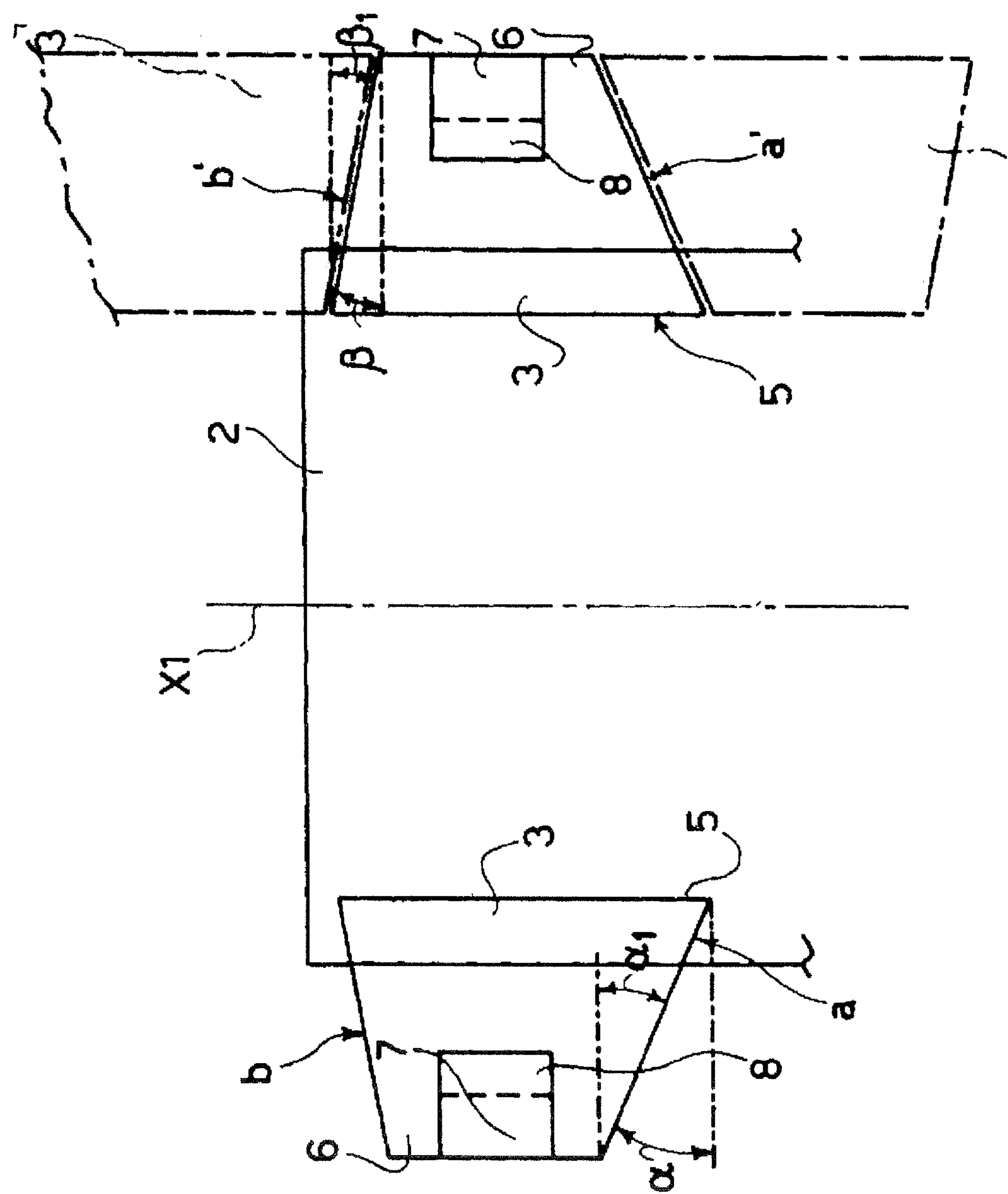
FIG. 2 is a schematic representation of the end of the article illustrated in FIG. 1 designed to highlight more clearly the geometrical characteristics of the solution described herein.
Figure 3:
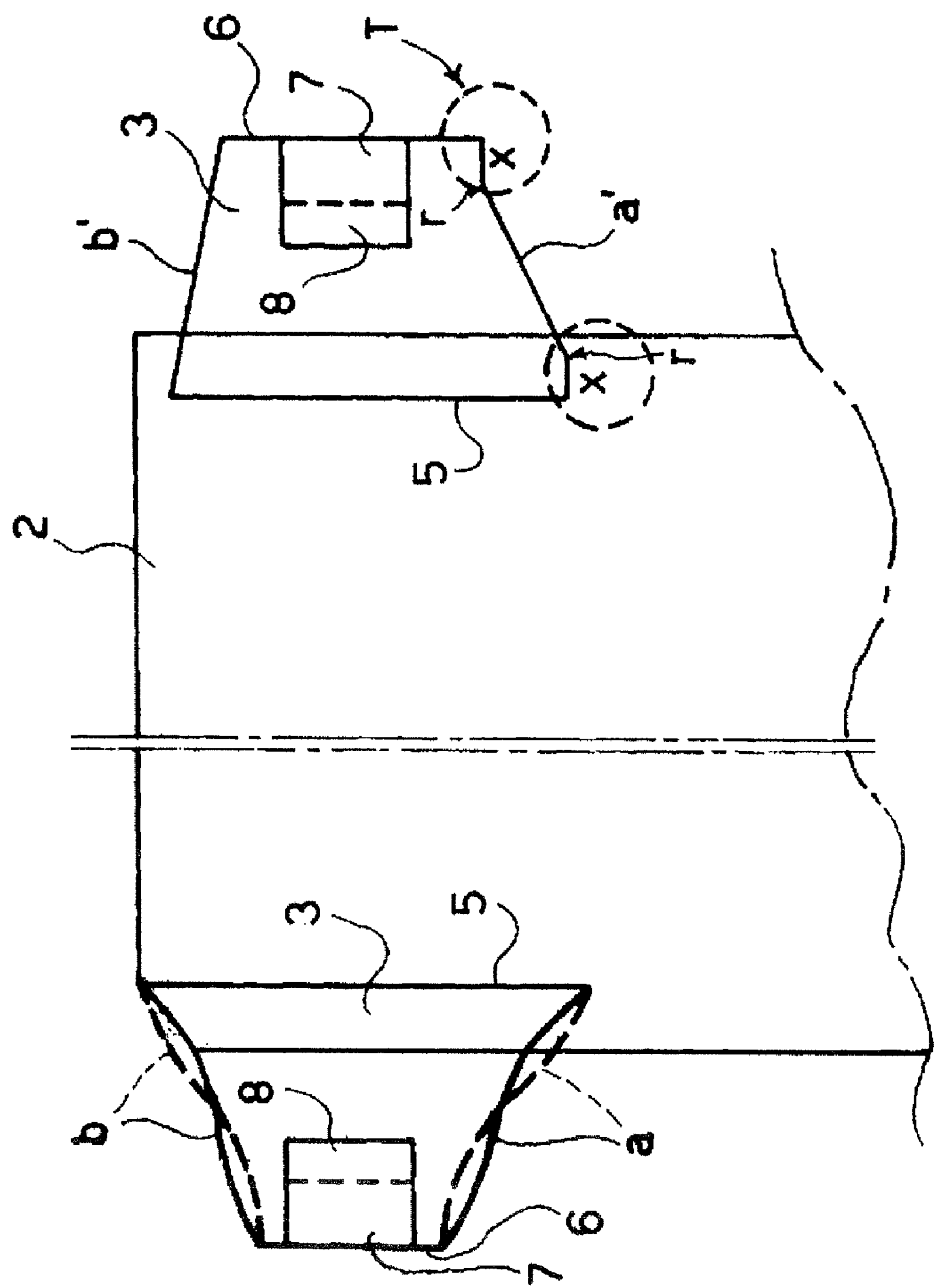
Figure 4:
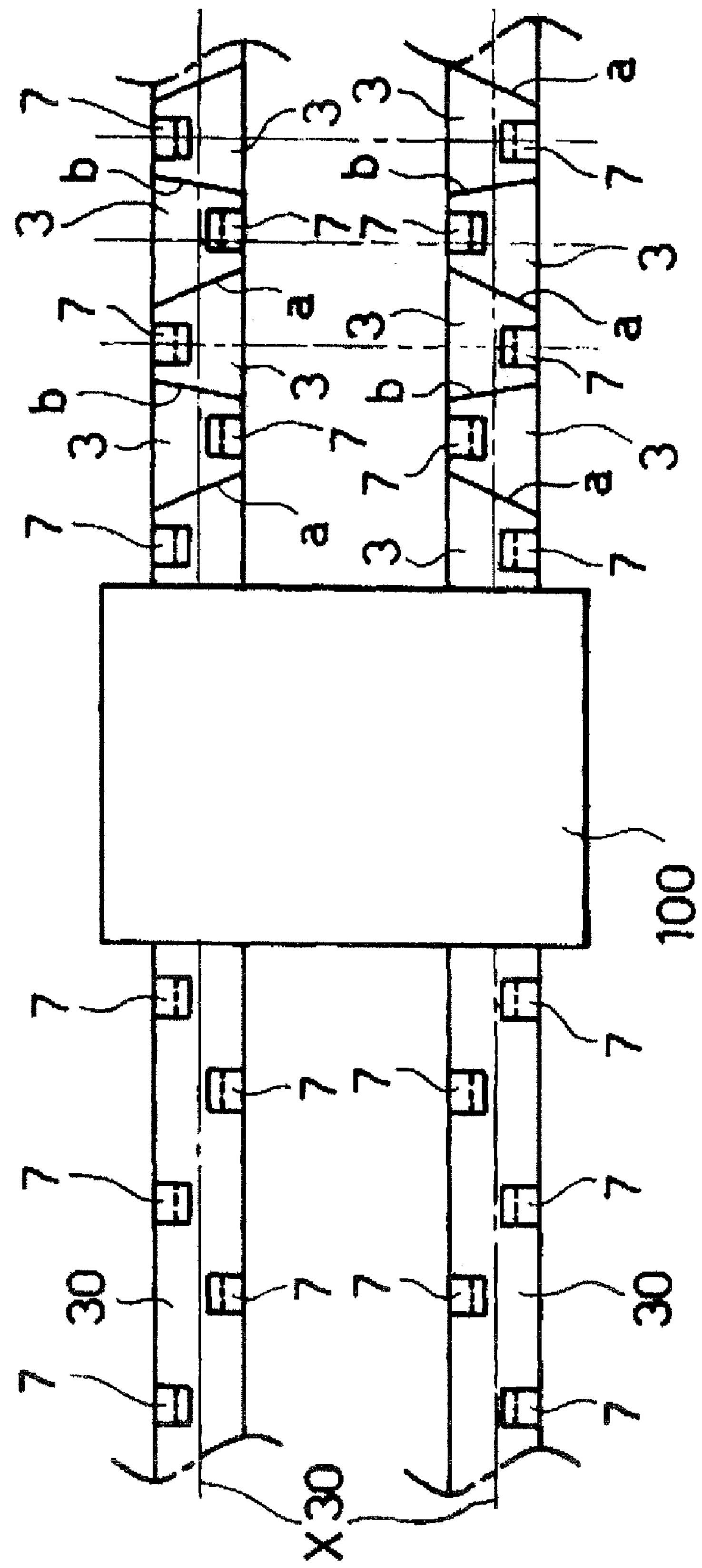
Figure 5:
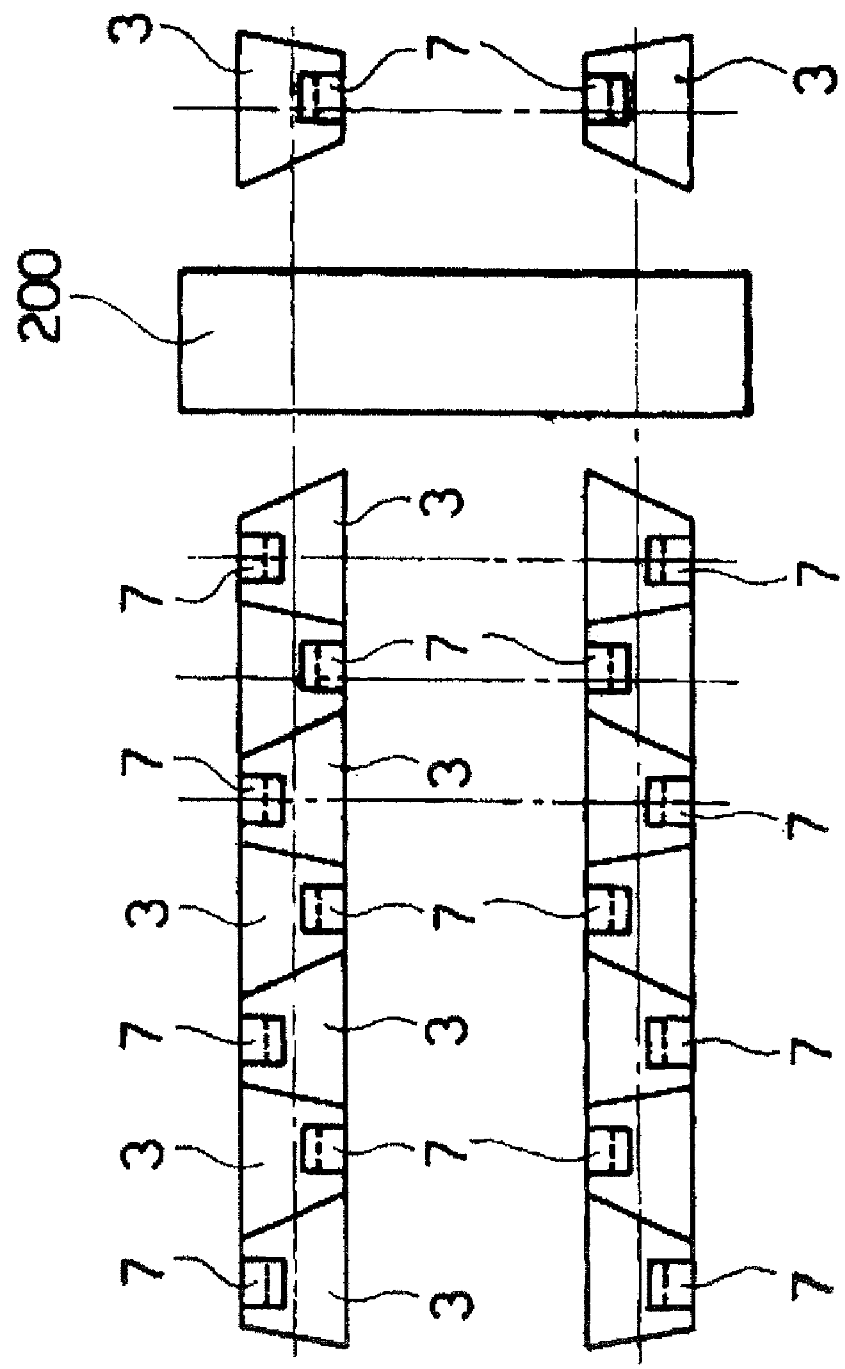
Figure 6:
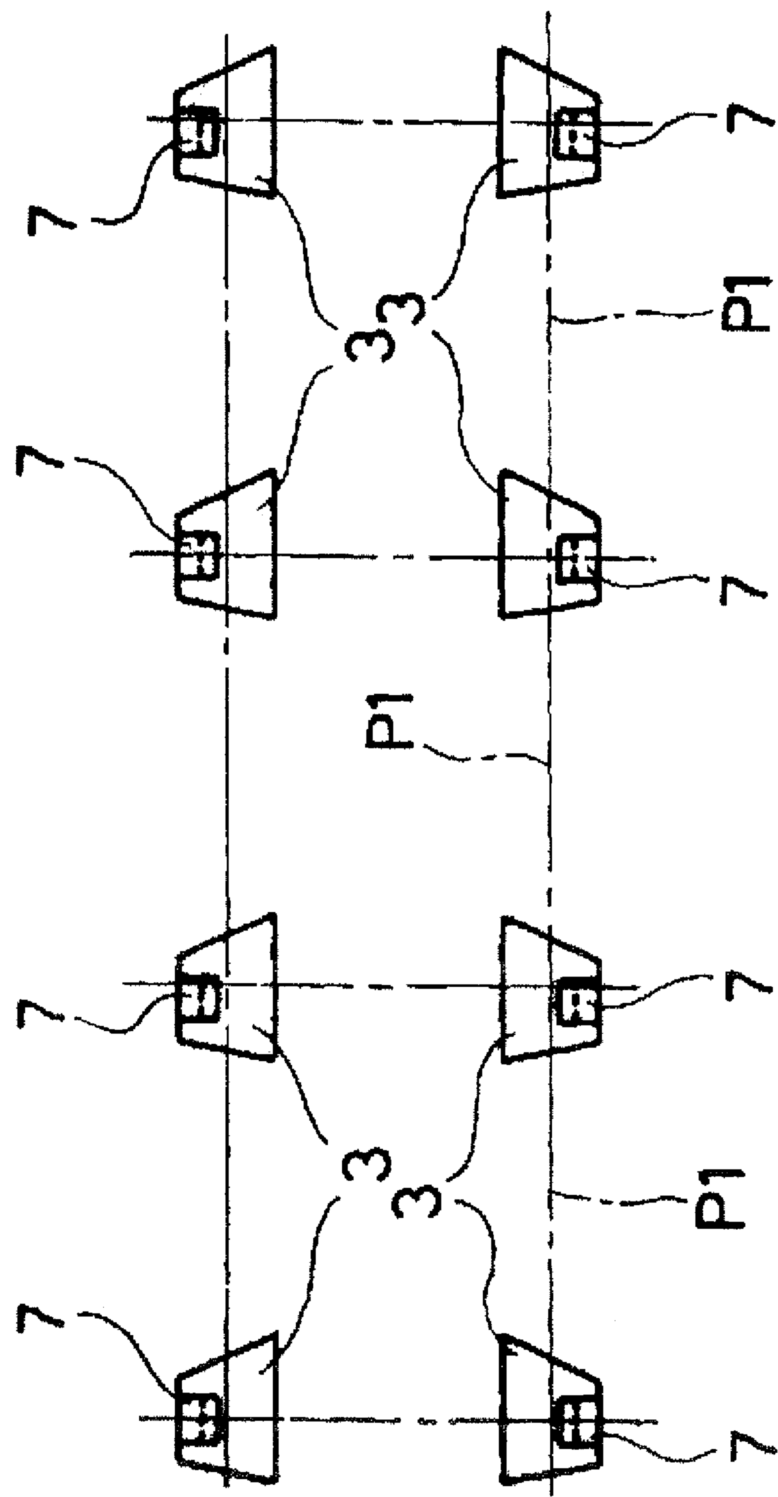
Figure 7:
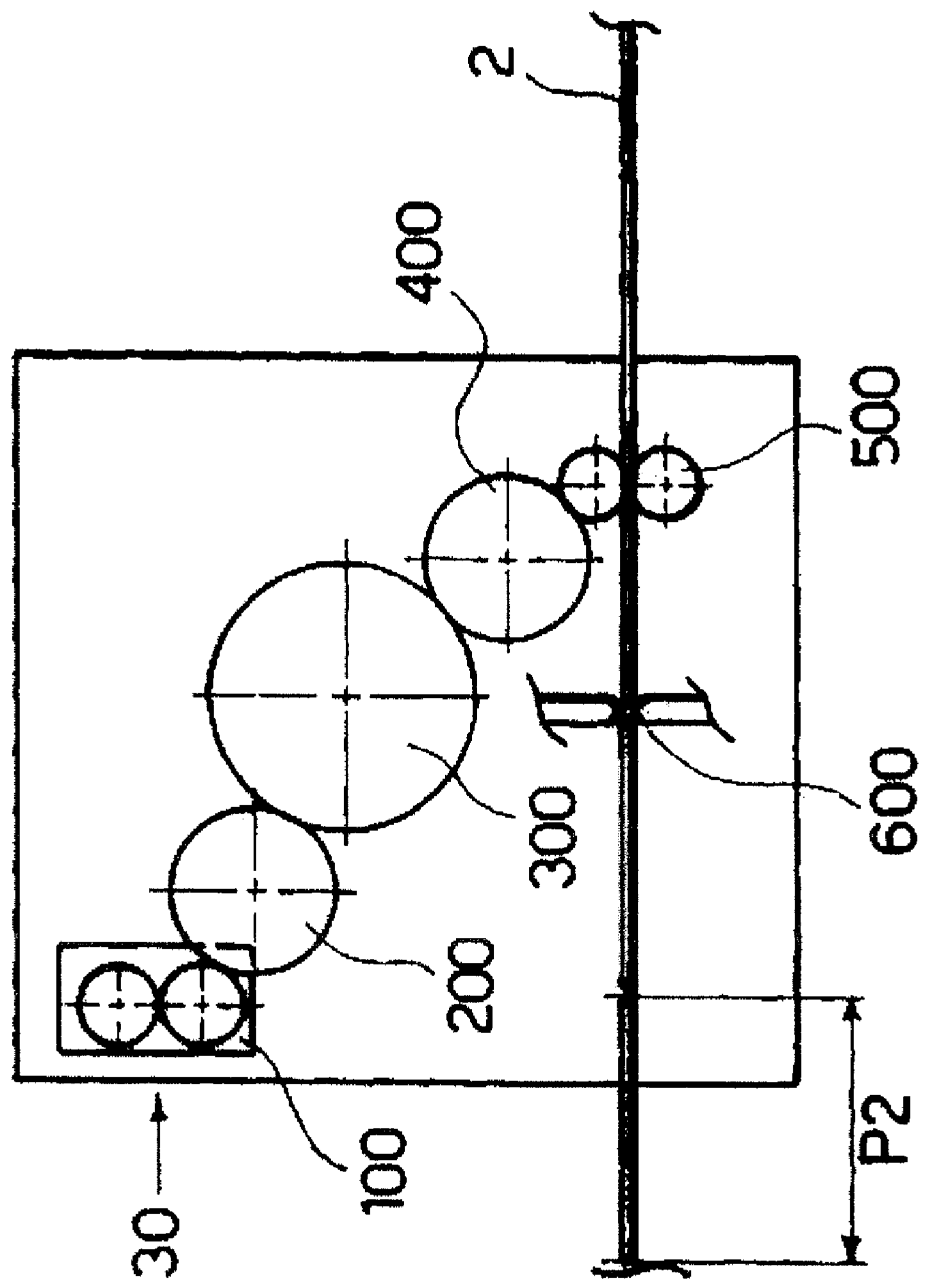

FIG. 3 further illustrates possible developments of the solution represented in FIG. 2;

FIGS. 4 to 6 illustrate successive steps of the method of production and of application of the side panels of the type described herein; and FIG. 7 is a general side elevation of a plant usable for implementation of the steps of the method to which FIGS. 4 to 6 refer.

DETAILED DESCRIPTION OF EXEMPLARY EMBODIMENTS

Figure 1:
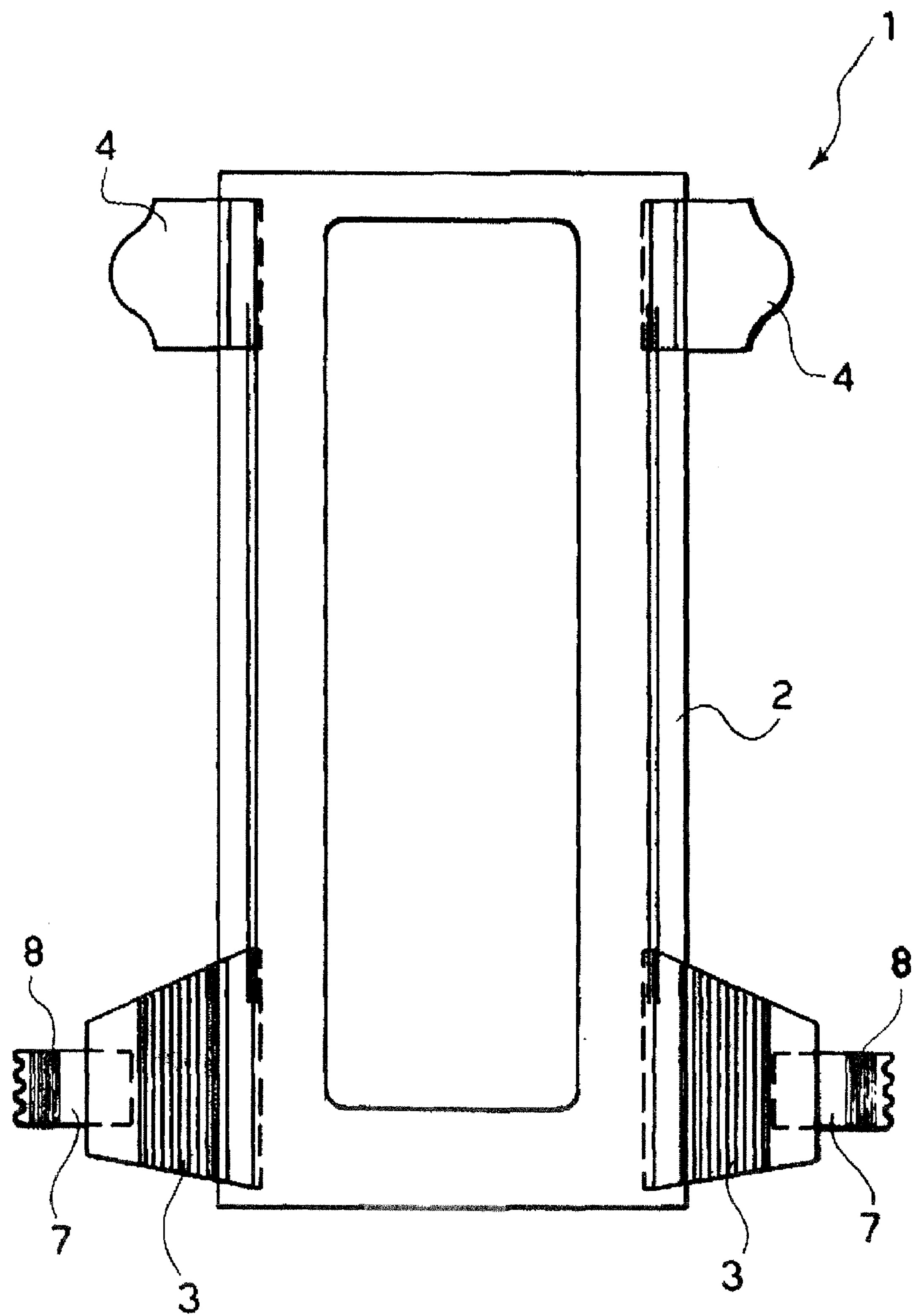
FIG. 1 is a general plan view of a sanitary article that can be worn as pants, provided with side panels of the type described herein, represented in the splayed-out condition.

FIG. 1 of the annexed plate of drawings is a schematic illustration of a sanitary article 1 of the type that can be worn as pants.

Just to clarify the general idea, and without any intention of limiting the scope of the invention, the article 1 can be a pair of diapers or training pants for babies.

The article 1 is here represented in a splayed-out condition and comprises, according to a general conformation to be deemed in itself known:

- a main body 2 constituted by a rectangular element, which can be set to form a U according to a general hollowed conformation around the perineal area of the user;
- two side panels 3 that project on opposite sides of one of the ends of the main body 2 so as to bestow upon the article 1 as a whole, viewed in a position where it is splayed out in the plane, a general T-shaped configuration; and
- two further side panels 4 that project from the end of the main body 2 opposite with respect to the end from which the side panels 3 project.

The specific characteristics of the main body 2 are not in themselves important for the purposes of description and understanding of the solution described herein. It will suffice to recall, by way of summary, that the main body 2 usually comprises:

- a topsheet, which is permeable to body fluids, designed to be set facing the body of the user;
- a backsheet, designed to be set facing the outside of the article (i.e., in a position opposite to the body of the user); and
- a layer made of absorbent material, set between the topsheet and the backsheet.

In general, the article 1 is designed to be worn with the hollow or U-shaped main body 2 in the general condition where it constitutes a crotch portion around the perineal region of the user, the end from which the elements 4 project is located on the front of the user, and the end from which the side panels 3 project is located in a position corresponding to the base of the spine of the user. The side panels 3 can thus extend on the sides of the user in order to come to connect up—typically adhesively or by means of a contact closing of the hook-and-loop type—to the elements 4.

As is well known to persons skilled in the art, in addition to said elements in the main body 2 there are usually present numerous accessory elements, such as elastication elements, layers for acquisition of body liquids (the so-called "acquisition layers"), etc. All this also applies as regards the details of production of the topsheet, backsheet, and absorbent core, according to a practically infinite range of possible variant embodiments. The description provided herein concentrates principally upon the characteristics of the side panels 3. It follows that, as the conformation and characteristics of the main body 2 vary, also the conformation and characteristics of the side elements 4 can vary within a wide range, as documented in the technical literature.

On the other hand, the side elements 4 may even be absent, it being in this case envisaged that the side panels 3 will engage directly with their distal ends the end of the main body 2 set on the front of the user. Even though this solution is hardly ever used in the art, the side panels 3 could be possibly located on the end of the main body 2 that is to be set on the front of the user.

Furthermore, in the case of articles sold "pre-fastened", i.e., "pre-closed" like the articles referred to as "training pants", panels are usually provided both in a position corresponding to the front end and in a position corresponding to the rear end of the main body 2 of the absorbent article 1. In this case, the side panels provided on each side of the article are connected to one another in a position corresponding to the respective distal edges.

As will be better appreciated from the view of FIG. 2, which constitutes a schematic representation of the end of the main body 2 in a position corresponding to which the side panels 3 are located, the panels 3 themselves have, in a possible embodiment shown in FIG. 2, the shape of a scalene trapezium.

The panels 3 are designed to be connected to the main body 2 according to known modalities—for example via heat-sealing or gluing, for example with glue of the hot-melt type—and are made of an elastic/elasticated material with characteristics of transpirability: in regard to these aspects see, for example, U.S. Pat. No. 6,572,595 or U.S. Pat. No. 6,994,761.

The side panels 3 hence present a generally tapered pattern starting from their proximal edge 5, connected to the main body 2, towards their distal edge 6. In a position corresponding to said distal edge, applied on the panel 3 is a connection formation 7, constituted, for example, by a label initially folded back and closed to form a U on the side panel 3 (see FIG. 2) and that can be freely splayed out towards the outside of the side panel 3, as may be seen more clearly in FIG. 1 so as to bear an attachment formation 8, provided at the projecting distal end of the label 7 to project freely towards the outside beyond the distal edge 6 of the side panel 3, the purpose being to bring the attachment formation 8 to couple (adhesively, or as a result of a hook-and-loop connection) with the corresponding element 4 or with the front portion of the main body 2 of the article 1.

The side panels 3 are hence identical to one another and designed to be exposed on the two opposite sides of the main body 2 of the article 1 in conditions of specular symmetry with respect to the principal longitudinal axis X1 of the article 1.

The major and minor bases of the scalene trapezium identify then the proximal edge 5 and the distal edge 6 of the panel 3, respectively.

From FIG. 2, within each panel 3 there may be distinguished an inner side a, a' (facing the inside of the article 1 and designed to occupy the bottom position in the article 1 when this is worn by the user), which forms an angle $\alpha$ with respect to the direction orthogonal to the principal axis X1.

Within each panel 3 there may then be distinguished an outer side b, b' (facing the outside of the article 1 and designed to occupy a top position in the article 1, when this is worn by the user), which forms an angle $\beta$ with respect to the direction orthogonal to the antero-posterior principal axis X1 of the article.

In the embodiment referred to in FIG. 2, the sides a, a' and b, b', albeit inclined with respect to the axis X1, are rectilinear. It follows that the angles $\alpha$, $\alpha_1$ and $\beta$, $\beta_1$ form two pairs of angles, equal to one another, in so far as they are alternating internal angles of two parallel straight lines cut by a straight line.

An important characteristic of the solution described herein lies in the fact that, even though the angles $\beta$ and $\beta_1$ could tend to 0, thus being perpendicular with respect to the axis X1, the choice of a value different from 0 (in particular, it will be noted that the relation $\beta=\beta_1<\alpha, =\alpha_1$ applies) facilitates manufacture of the elements 3 resorting to traditional mechanical knives.

Of course, cutting of the sides a, a' and b, b' can be performed using laser techniques.

The representation of FIG. 3 (where parts and elements that are identical or equivalent to the ones already described with reference to FIG. 2 are designated by the same reference numbers appearing in FIG. 2) shows how it is possible to make side panels 3 with shapes even more complex than the general scalene-trapezium conformation represented in FIG. 2.

For example, the left-hand part of FIG. 3 illustrates the possibility of making the panels 3 with end sides a and b, which are as a whole inclined with respect to the general direction of extension of the proximal edge 5 and distal edge 6, whilst having, however, an S-shaped pattern.

In particular, illustrated in the left-hand part of FIG. 3 is the possibility of obtaining said S-shaped pattern according to two possible variants, illustrated, one with a solid line and the other with a dashed line. The two variants differ in that:

- in the first case (solid line), the S-shaped path is such that the profile of the edges a and b is concave in the proximity of the proximal edge 5 and convex in the proximity of the distal edge 6; and
- in the second case (dashed line), the S-shaped path is such that the profile of the edges a and b is convex in the proximity of the proximal edge 5 and concave in the proximity of the distal edge 6.

In the right-hand part of FIG. 3 in the side ends of the panel 3 there are visible, as regards the inclined sides or edges a, a', stretches T provided in the proximity of the bases and 7. Instead of following the general inclined pattern of the side a, a' as a whole, the stretches T are perpendicular to the side edge of the main body 2 (hence, perpendicular to the axis X1). In addition to presenting a number of advantages from the aesthetic standpoint, this choice means that the side panel 3 does not present particularly acute parts of angle, which tend to be rather flexible, whilst the stretches T represented in FIG. 3 have a certain consistency and do not run the risk of undergoing deformation in an undesirable way during the process of production and application of the side panels 3.

The panels 3 arranged on the two sides of the body 2 will usually present the same geometrical shape so as to give rise to a general specular symmetry with respect to the principal axis X1.

Illustrated schematically in FIG. 2, with reference to the side panel 3 represented to the right, is an important characteristic of the panels 3 themselves.

That characteristic is common to all the embodiments illustrated herein and, as will be seen more clearly in what follows, has the advantage of eliminating the production waste of the side panels.

According to that characteristic—whatever the specific pattern of the sides a, a', b, b' (i.e., rectilinear, as in the case of FIG. 2, or else S-shaped or with a mixed-line pattern as in the case of FIG. 3 or in the case of other variant embodiments not specifically illustrated)—each panel 3 may be juxtaposed, without any solution of continuity (i.e., without leaving spaces or voids), with two similar panels 3 (said profile being indicated by a dashed-and-dotted line in the right-hand part of FIG. 2) rotated through 180° in the plane of the panel itself.

Expressed even more simply (see once again the right-hand part of FIG. 2), the panels 3 are made, in a position corresponding to the sides a, a', b, b' that define the tapered pattern thereof, in such a way that, if a first panel 3 is taken, oriented in a direction (i.e., as viewed in FIG. 2, with the pattern of the tapering from left to right), and another two similar panels 3 are taken, oriented, however, with the tapering in the opposite direction, i.e., rotated through 180° in the general plane of the panel, these latter two panels rotated through 180° (see the corresponding profile represented with a dashed line in the right-hand part of FIG. 2) can be juxtaposed with the first panel 3, without leaving spaces or voids, i.e., without giving rise to any solution of continuity between the juxtaposed panels.

FIG. 4 illustrates a first step of a possible method for producing (and, possibly applying on the respective sanitary articles) side panels 3 of the type described previously.

In FIG. 4, the reference number 30 designates a web of the material designed to constitute the panels 3 (i.e., an elasticated material with, preferentially, characteristics of "breathability"—of a known type) applied on which are, on one side and on the other, with a spacing pitch equal to the average length of the element 3 in the direction of the bases 5 and 6, connection formations 7, such as, for example, the labels bearing the adhesive or hook-and-loop formations of attachment 8, to which reference has already been made previously in relation to FIGS. 1 and 2.

Usually, the labels 7 can be folded back on the opposite edges of each web or strip 30 according to a general V-shaped configuration so as not to project appreciably with respect to the web 30 itself, which is to be subjected, in a shaped-cutting unit 100, to an operation of cutting with the characteristics described in greater detail in what follows. Application of the labels 7 on the web 30 is performed according to criteria in themselves known, which do not require any further detailed description herein. In this regard, it will be appreciated in particular that the preparation of the web 30 with the labels 7 applied on the opposite edges of the web in staggered positions is suited to being performed both as a step of an "on-line" process, performed at a preliminary level with respect to the subsequent operations that will be explained in what follows, and in the form of an "off-line" operation, performed at points in time and/or space different from those of the subsequent operations.

Represented in FIG. 3 are two strips 30, which advance towards the cutting unit 100 set alongside one another, moving from left to right, as viewed in FIG. 4. This solution is preferred in so far as it enables availability, as will be seen more clearly in what follows, of two arrays or chains of side panels 3 that can be applied on the two opposite sides of one and the same sanitary article (see for reference FIGS. 1 and 2).

The cutting unit 100 (which can be either a mechanical cutting unit, for example one with rotary knives, or a laser cutting unit, for example of the type described in EP-A-1 447 068 or in the European patent application No. 05425450.3) enables cuts to be obtained, in each of the strips 30, in a position between the labels 7, which—whatever their specific shape or path—are roughly oblique with respect to the direction of advance of the strips 30. These cuts are designated in FIG. 4 by the references a and b and correspond precisely to the edges of the panels 3 designated by a, a' and b, b' in FIGS. 2 and 3.

The cutting unit 100 intervenes on each web or strip 30 so as to perform, in alternating sequence:

- first cuts (a) that form, with respect to the longitudinal axis X30 of the web 30, the angle of inclination $\alpha$, to which reference is made in FIG. 2; and
- second cuts (b) that form, once again with respect to the longitudinal axis X30 of the web 30, the angle of inclination $\beta$, to which reference is made in FIG. 2.

When, as in the case illustrated, a cutting unit 100 is used, designed to operate in parallel on two strips 30, both the movement of advance of the strips 30 and the course of the operations of cutting on the two strips are synchronized in such a way as to cause, as will immediately be appreciated better from the right-hand part of FIG. 4, the cuts a and b to be made in a symmetrical way, hence giving rise, if ideal reference is made to the two cut strips that emerge from the cutting unit 100, to two chains of panels 3, where:

- within each web 30 cut, the two chains of panels 3 can be seen as a sequence of panels 3 the one rotated through 180° with respect to the preceding (and to the subsequent) one in the general plane of the panels 3—all this, of course, without there being created any solution of continuity between adjacent panels 3; and
- considering the mutual arrangement of the panels 3 in the two chains, each panel 3 with the major base 5 facing the other chain has in front of it and facing it, at one and the same degree of advance, the major base 5 of another panel 3 and, in a dual way, each panel 3 with the minor base 6 (bearing a label 7) facing the other chain has in front of it and facing it, at one and the same degree of advance, the minor base 6 of another panel 3.

Even though FIG. 4 makes reference—for reasons of simplicity of illustration—to cuts a, b with a rectilinear pattern, it is altogether evident that upon the aforesaid cuts there may in actual fact be imparted (an operation that in general is very easy to perform in the case where the unit 100 is a laser cutting unit) a path that may be in practice arbitrary—just to provide one example: one of the S-shaped paths illustrated in the left-hand part of FIG. 3. At the same time, precisely on account of the criteria with which the various panels 3 are cut out within the strips 30, the basic characteristic already recalled previously is maintained such that each panel 3 is juxtaposable without any solution of continuity (i.e., without leaving spaces or voids) with two homologous panels turned over through 180° in the general plane of the panel.

Once again from the right-hand part of FIG. 4, it will be appreciated that, within each web 30 that exits from the cutting unit 100 it is possible to recognize an alternating sequence of:

- first panels 3, in which the shorter base 6, bearing the label 7, is already correctly facing the outside of the complex of the two strips 30 and has already the correct orientation for its location on two opposite sides of a sanitary article such as the article 1 of FIG. 1; and
- second panels 3, in which the shorter base 6, bearing the label 7, is instead facing the inside of the complex of the two strips 30: in order to be located on two opposite sides of a sanitary article, such as the article 1 of FIG. 1, said second panels 3 require being rotated through 180° in their plane of lie.

It will, on the other hand, be appreciated that the same result that may be obtained by rotating the panels through 180° in their plane of lie can be obtained by reversing or overturning the aforesaid panels, i.e., so that the face of the panel situated originally in the top position will end up occupying one in the bottom position, and vice versa. This result can be obtained, for example, by overturning the panels 3 through 180° about their longitudinal central axis, parallel to the edges 5 and 6.

The experiments conducted by the present applicant show that the rotation through 180° in the plane of lie currently constitutes a preferred solution. The sequel of the description will hence make reference to said solution, which involves rotation of the panels in their plane of lie.

Of course, in order to be able to carry out this operation of rotation of one panel out of two, precisely because the panels 3 exit from the cutting unit 10 juxtaposed without any solution of continuity, it is necessary to proceed to setting the various panels 3 apart in their direction of advance.

The above operation, on the other hand, becomes in any case necessary in view of the subsequent application on the central body 2 of corresponding sanitary articles, such as the article 1 of FIG. 1.

More precisely, in order to proceed to application of the panels 3 on corresponding sanitary articles 1, it is necessary to carry out two operations:

- rotate one panel 3 out of two through 180° in its plane of lie; and
- space apart from one another the panels 3 that exit from the cutting unit 100 with a pitch of separation corresponding to the length of the articles on which said panels are to be applied.

As regards the operation of spacing (or to use a term widely adopted in the sector, "repitching"), two basic considerations are involved:

- the spacing applied to the panels 3 must of course be greater than a minimum value such as to enable one panel 3 to be rotated with respect to the panel that precedes it and to the panel that follows it, without interfering therewith; and
- the final pitch of application on the articles must be able to vary as a function of the characteristics of the article considered (the so-called "change of format"): to provide an evident example, the spacing pitch required, for example in the case of diapers for babies, is certainly smaller—even much smaller—than the spacing pitch required, for example, in the case of sanitary towels for incontinent adults.

The dynamics of the operation of "change of format" necessary for adapting the spacing pitch of the panels 3 to the dimensions of the corresponding articles is rather wide: for example, the spacing pitch required for the application on the article may easily range between 360 mm and 600 mm.

The aforesaid operations of "repitching" and rotation of the panels 30 through 180° in their plane of lie can be performed by resorting to equipment in itself known. For example, just to limit our considerations to the patent documents filed in the name of the present applicant, as regards the operation of repitching it is possible to resort, for example, to the solutions described in EP-A-1 179 495 and in the European patent application No. 05425692.0.

As regards, instead, the movement of rotation through 180°, it is possible to resort, for example, to a development of the solution described in EP-A-0 997 123. Of course, in referring to said prior patent document, it must be taken into account that, in the solution described in said prior document, all of the gripping elements designed to act on the articles subjected to rotation are configured in such a way as to effect a movement of rotation. In the specific case considered here, it will of course be envisaged that, the modes of gripping on the panels 3 remaining unvaried, the rotary device will be configured in such a way that one gripping element "shoe" out of two will remain fixed, without rotating, since the movement of rotation must be applied only on one panel out of two.

It will again be appreciated that the representation of the function of rotation of the device 300 provided in FIG. 6 is deliberately simplified. In the case of elasticated panels for articles of a training-pant type (which reach the user "pre-fastened", i.e., "pre-closed"), the device 300 must be devised (according to criteria in themselves known) so that each series of gripping units "shoes" acting on the panels 3 will have a fixed gripping element and a rotating gripping element, set alternately between one series and another: if two rotating gripping elements were installed both on the same series, on account of the greater length of the elasticated panels of the training-pant articles, during rotation there would be interference between the gripping elements themselves. The greater length of the elasticated panels on the training-pant articles is due, as is known, to the fact that these panels must be applied both at the rear and at the front with respect to the article.

In principle, the operations of repitching and rotation of one panel 3 out of two could be performed, for example, bringing first the panels 3 to the final desired spacing pitch, and then proceeding to rotation of one panel out of two according to the modalities described previously.

The above desired result is achieved using just two units, namely, a repitching device (which can be of an adjustable type, i.e., such as to enable selective variation of the pitch of separation of the articles at output) and a rotary device, arranged cascaded to one another.

The present applicant has found that, in contradiction to this evident approach, it is advantageous to proceed by carrying out first a repitching of the panels 3 with a pitch P1 that is much larger than what in itself would be required to prevent the panels 3 from interfering with one another during rotation through 180° of one panel out of two.

As illustrated schematically in FIG. 5, the first repitching operation is performed downstream of the cutting unit 100 with a repitching device 200 such as to fix a pitch of separation of the panels 3 at output therefrom of a value chosen, for example, within a range of between 70 and 100 mm. This first pitch P1, at output from the unit 200, is in general a fixed pitch, i.e., a pitch maintained at the value indicated above independently of the final pitch desired for the panels 3.

In other words, the first repitching device 200 operates in such a way as to separate the panels 3 by a distance P1, for example, in the region of 70-100 mm, both in the case where they are panels 3 designed to be applied on baby diapers and in the case where the panels 3 are designed to be applied on sanitary towels for incontinent adults.

Once this first repitching operation with a fixed pitch P1 (referred to in FIG. 5) is implemented, the panels 3 thus spaced apart are fed to a rotation unit 300 (see FIG. 8) that carries out overturning or rotation through 180° of one panel 3 out of two.

The corresponding operation of orientation is such as to bring all the panels 3 to assume the same orientation, i.e., with the shorter distal sides 6 on which the labels 7 are applied facing outwards.

At output from the rotary device 300 of FIG. 7 there will then be available a sequence of panels 3, as illustrated schematically in FIG. 6, i.e., panels 3, which, within each longitudinal row, have the same orientation, with the labels 7 facing outwards and with a spacing pitch P1 that is the (fixed) one imparted by the unit 200.

At this point, the panels 3, oriented according to the final desired orientation, are fed to a further repitching unit 400, which is also made according to criteria in themselves known, i.e., according to the criteria already recalled previously with reference to the repitching assembly 200.

An important difference is that, whereas the repitching unit 200 is configured in such a way as to bring the panels 3 at output therefrom to have a separation pitch P1 that is fixed, the repitching unit 400 is made in such a way as to be able to enable selective variation of the pitch of separation between successive panels 3 according to the specific needs of application on the respective sanitary articles.

In particular, this "final" pitch of separation corresponds, as illustrated schematically in FIG. 8, to a value of pitch P2 corresponding in effect to the overall length of the individual article on which the panels 3 are applied (for example, 360 to 600 mm).

The fact of performing the spacing of the panels 3 in two steps, first separating them with a fixed pitch P1 and then adjusting (after rotation of one panel out of two) the pitch of separation to the desired value P2 enables both exploitation of the motor of the repitching unit 400 to be optimized and the operation of adaptation ("change of format") to be rendered more convenient when the dynamics of variation of the final pitch P2 becomes particularly wide.

Assuming—of course merely by way of example—that it is necessary to take into account possible variations of the pitch P2 in the range between 360 and 600 mm, there may be hypothesized, for example, a solution in which the first repitching unit 200 brings the pitch P1 between the panels 3 to a (fixed) value of 70 to 100 mm.

Any adaptation (if necessary) to values of the pitch P2 different from the value of P1 is then entrusted to the second repitching unit 400. This intervention can, for example, require the unit 400 to "gain", starting from a value of P1 of, for example, 100 mm, another 260 to 500 mm required to arrive (according to the article on which the panels are applied) at a pitch P2 comprised in the range between 360 and 600 mm.

As an alternative (according to the specific needs of implementation and of the ranges of articles that it is intended to produce), it is also possible to envisage configuring the first unit 200 in such a way as to cause the pitch P1 to be such that the second repitching unit 400 will perform its function not in the sense of an increase of the spacing (for example to "gain" more millimetres of separation, as in the case considered previously, to reach a final value of P2 that is greater than P1), but in the sense of a decrease (for example, to "lose" a few millimetres of separation to reach a final value of pitch P2 that is smaller than P1).

Added to this is the possibility of varying the final value P2 without performing any intervention of replacement of parts in the complex of the units 200, 300 and 400, represented in FIG. 8, but by acting exclusively, usually via software, on the adjustment of the corresponding unit.

Once the desired pitch P2 has been reached at output from the repitching unit 400, the panels 3 are available for being applied on the main body 2 of the sanitary articles.

FIG. 7 refers to a situation (the most common one at the current industrial level) in which the body 2 is still in the form of a single strip, on which, in an application unit 500 (of a known type), the panels 3 are applied for example via thermomechanical sealing. Usually, the unit 500 sees also, in a known way, to overturning the panels 3 on top of the main body 2 of the article 1 so as to minimize the encumbrance thereof in view of packaging.

At this point, the individual articles thus completed advance towards a cutting unit 600 (for example, with reciprocating or rotary knives), which sees to separating the individual articles from one another, completing the process of production thereof.

It will be appreciated that, even though the method illustrated with reference to the sequence of FIGS. 4 to 6 has been developed according to the need to treat side panels in which the profile of the sides a, a' and b, b' responds to the particular characteristics described previously, it can be used also to obtain repitching and selective rotation (one element out of two or, in general, one element out of n, or m elements out of n) of side panels, between which, after the operation of segmentation performed in the unit 100, there are present solutions of continuity.

Consequently, without prejudice to the principle of the invention, the details of construction and the embodiments may vary, even extensively, with respect to what is illustrated herein purely by way of non-limiting example, without thereby departing from the scope of the invention, as defined in the annexed claims.

The invention claimed is:

1. A method for manufacturing sanitary articles wearable as pants, said articles having a main body that can assume a general U-shaped configuration, with end parts arranged on the front and on the back of the body of the user, with at least one side panel for connecting said end parts on each side of the user, said at least one side panel having a proximal edge to be fixed on said main body and a distal edge carrying a connection formation for closing the article around the waistline of the user, the method comprising:

providing two webs of film material, said webs comprising two parallel strips with each strip of said strips comprising a longitudinal axis;

subjecting each of said strips to segmentation by symmetrically cutting each of said strips with cuts that are roughly oblique with respect to said longitudinal axis, so as to obtain, two chains of side panels wherein:

a) each panel of said panels of a chain of the chains, having a proximal edge facing the other chain of the chains has in front of each panel and facing each panel a proximal edge of a panel in the other chain; and b) each panel of said panels of a chain of the chains having a distal edge facing the other chain of the chains, and bearing a connection formation, has in front of each panel and facing each panel the distal edge, bearing a connection formation, of a panel in the other chain;

applying each connection formation in a staggered position on the opposite edge of each strip relative to each other connection formation with a spacing pitch equal to the average length of said panels in the direction of said longitudinal axis; and subjecting in each of said chains, said panel with a distal edge facing the other chain to an operation of rotation chosen between a rotation through 180° in the general plane of the panel and overturning of the panel; and applying said panels on the main body of said sanitary articles such that said proximal edge of each of said panels is connected to said main body of each of said sanitary articles.

2. The method according to claim 1, further comprising setting apart, with a given pitch of separation, the side panels in said chain before subjecting one side panel out of two in said chain to said operation of rotation.

3. The method according to claim 2, further comprising subjecting the side panels in said chain, after said operation of rotation, to a further repitching operation with a second pitch of separation.

4. The method according to claim 2, further comprising:

attributing to said given pitch a constant value; and varying selectively said second pitch according to the format of the sanitary articles on which said side panels are applied.

5. The method according to claim 4, further comprising rendering said second pitch larger than said given pitch.

6. The method according to claim 4, further comprising rendering said second pitch smaller than said given pitch.

7. A method for manufacturing sanitary articles wearable as pants, the method comprising:

providing two webs of film material, said webs comprising two parallel strips with each strip of said strips comprising a longitudinal axis and said strips adjacent each other;

symmetrically cutting each of said strips with cuts that are roughly oblique with respect to said longitudinal axis to segment the strips, so as to obtain two chains of side panels wherein:

a) each panel of said panels of a chain of the chains has a fixed connecting edge closest to and facing the other chain of the chains and facing a second fixed connecting edge of a panel in the other chain; and b) each panel of said panels of a chain of the chains has an extended edge closest to and facing the other chain of the chains and bearing a connection formation and facing a second extended edge, bearing a connection formation, of a panel in the other chain;

applying each connection formation in a staggered position on the opposite longitudinal edge of each strip relative to each other connection formation with a spacing pitch equal to the average length of said panels in the direction of said longitudinal axis; and subjecting in each of said chains, each panel with said extended edge facing the other chain to an operation of rotation chosen between a rotation through 180° in the general plane of the panel and overturning of the panel; and applying said panels on a main body that can assume a general U-shaped configuration, with end parts of said main body arranged on the front and on the back of the body of the user and having a fixed connecting edge connected to said main body and an extended edge carrying a connection formation.

* * * * *